(12) United States Patent
Heller et al.

(10) Patent No.: US 6,623,512 B1
(45) Date of Patent: Sep. 23, 2003

(54) CIRCADIAN RHYTHM RESET METHOD AND DEVICE

(75) Inventors: H. Craig Heller, Palo Alto, CA (US); Anthony N. van den Pol, Branford, CT (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/359,531

(22) Filed: Jul. 22, 1999

Related U.S. Application Data
(60) Provisional application No. 60/094,292, filed on Jul. 27, 1998.

(51) Int. Cl.[7] .................................................. A61N 5/06
(52) U.S. Cl. ............................. 607/88; 128/898; 600/26
(58) Field of Search ...................... 600/26–28; 315/158, 315/200, 203; 128/898; 607/89, 90, 91, 88

(56) References Cited

U.S. PATENT DOCUMENTS

| | | |
|---|---|---|
| 4,930,504 A | 6/1990 | Diamantopoulos et al. |
| 5,092,669 A | 3/1992 | Anderson |
| 5,304,212 A | 4/1994 | Czeisler et al. |
| 5,503,637 A | 4/1996 | Kyricos et al. |
| 5,545,192 A | 8/1996 | Czeisler et al. |
| 5,589,741 A * | 12/1996 | Terman et al. ............... 315/360 |
| 5,709,645 A | 1/1998 | Siever |
| 5,805,267 A * | 9/1998 | Goldman ..................... 351/203 |

OTHER PUBLICATIONS

Illnerová, H., et al., "Different Mechanisms of Phase Delays and Phase Advances of the Circadian Rhythm in Rat Pineal N–Acetyltransferase Activity" *J Biol Rhythms* 4(2):187–200 (1989).

Ralph, M.R., and Mrosovsky, N., "Behavioral Inhibition of Circadian Responses to Light" *J. Biol Rhythms* 7(4):353–359 (1992).

Reiter, R.J., et al., "A Single 1–or 5–Second Light Pulse at Night Inhibits Hamster Pineal Melatonin" *Endocrinology* 118(5):1906–1909 (1986).

* cited by examiner

*Primary Examiner*—Linda C. M. Dvorak
*Assistant Examiner*—R. Kearney
(74) *Attorney, Agent, or Firm*—Peter J. Dehlinger; Larry W. Thrower; Perkins Coie LLP

(57) ABSTRACT

A method for phase shifting the circadian pacemaker or treating seasonal affective disorder in a subject is disclosed. The method includes exposing the subject's eye region to a given-intensity light flash having a flash duration of between about 1–500 msec, at a periodicity of at least about one flash per minute, over a selected time period effective, were the subject exposed to a continuous light pulse of the same intensity for this period, to phase shift the circadian pacemaker or treat the seasonal affective disorder in the subject. Also disclosed is a device for practicing the method.

3 Claims, 2 Drawing Sheets

CIRCADIAN RHYTHM RESET METHOD AND DEVICE

This application claims the benefit of U.S. provisional patent application Serial No. 60/094,292, filed Jul. 27, 1998.

This invention was made with Government support under contract F49620-93-1-0283-P00003 awarded by the Air Force Office of Scientific Research. Accordingly, the Government has certain rights in this invention.

FIELD OF THE INVENTION

The present invention relates a method and device for resetting a subject's circadian pacemaker or for treating other sleep or seasonal affective disorders.

REFERENCES

Hendrickson, A. E., et al., *Z. Zellforsch mikros Anat.* 135:1 (1972).

Johnson, C. H., AN ATLAS OF PHASE RESPONSE CURVES OF CIRCADIAN AND CIRCATIDAL RHYTHMS, Vanderbilt Univ, 1990.

Moore, R. Y., et al., *Brain Res.* 42:201 (1972a).

Moore R. Y., et al., *J. Comp. Neurol.* 146:1 (1972b).

Stephan, F. K., et al., *Proc. Nat. Acad. Sci. USA* 69:1583 (1972).

BACKGROUND OF THE INVENTION

Most animals have daily rhythms of behavior and physiology. These rhythms free-run with periodicities close to 24 hours (circadian) in the absence of environmental cues. Circadian rhythms are generated by endogenous pacemakers that can be entrained to the 24 hour day by external physical cues. Entrainment by external cues involves phase shifting the rhythm of the endogenous pacemaker to bring it into synchrony with normal geophysical cues. The most important entraining stimulus is exposure to light. For example, exposure to light in the early dark period (circadian time $CT_{12}$–$CT_{18}$) will phase delay the pacemaker, and exposure to light in the late dark period ($CT_{18}$–$CT_{24}$) will phase advance the pacemaker (Johnson).

The circadian clock is important in the regulation of many circadian rhythms, including regulation of pineal gland metabolism, and melatonin secretion. In mammals, the circadian pacemaker resides in a group of hypothalamic neurons, the suprachiasmatic nucleus (SCN) (Moore, 1972a; Stephan) that receives direct connection from retinal ganglion cells (Hendrickson; Moore, 1972b).

Most people have a circadian cycle of about 24 hours, with variations of up to one hour in either direction being common. Under normal light cycles, these cycles are maintained in synchrony with normal geophysical cues. However, when a person fails to receive normal light cues, particularly due to light deprivation as occurs in winter months at extreme latitudes, or in heavily overcast environments, the circadian clock can free-run out of synchrony with the environment, causing sleep disorders, depression, and other symptoms classed generally as seasonal affective disorder (SAD). A common treatment for SAD is to expose the subject to high-intensity visible light for periods of 2–3 hours in the early morning. This treatment is usually carried out with banks of fluorescent lights.

It would be desirable to provide a method and device for treating SAD without the need for special high-intensity lighting, and without the requirement for long exposure to high-intensity of light.

A person's circadian cycle must also be reset when travelling between time zones. There are ways that readjusting to a new day/night light cycle can be accelerated, but in general, the process is one of slowly readjusting to the new time zone through a period of "jet-lag".

It would be desirable to provide a method and device that would allow a traveller to systematically and relatively quickly adjust his or her circadian clock to a new time zone.

SUMMARY OF THE INVENTION

In invention includes, in one embodiment, a method of phase shifting the circadian pacemaker or treating seasonal affective disorder in a subject. The method includes exposing the subject's eye region to a given-intensity light flash having a flash duration of between about 1–500 msec, at a periodicity of between about one flash per 5 to 60 secs, i.e., 1 to 20 times per minute, over a selected time period effective, were the subject exposed to a continuous light pulse of the same intensity for this period, to phase shift the circadian pacemaker or treat the seasonal affective disorder in the subject.

The flash duration is preferably between about 1–25 msec (milliseconds), more preferably between about 1–5 msec.

The period of exposure is typically between about 5–180 minutes, typically 15–150 minutes. The total exposure time may be in the range as low as 120–600 msec, for example, 2 msec flashes, 2 per minute, over a 30 minute period (120 msec), or 2 msec flashes, 5 per minutes, over a 60 minute period (600 msec).

For use in phase advancing the subject's circadian pacemaker, and for treating SAD, the exposing is preferably carried out during the subject's circadian time $CT_{18}$ to $CT_{24}$, preferably $CT_{22}$ to $CT_{24}$. For use in phase retarding the subject's circadian pacemaker, the exposing is preferably carried out during the subject's circadian time $CT_{12}$ to $CT_{18}$, preferably $CT_{12}$ to $CT_{14}$.

In another aspect, the invention includes a device for phase shifting the circadian pacemaker or treating seasonal affective disorder in a subject. The device includes a visible light emitter adapted to be supported at a position to provide a light exposure to the subject's eyes, a control unit for activating the light emitter to emit a light flash of a given intensity having a flash duration of between about 1–500 msec, at a frequency of at least about one flash per minute, over a selected time period effective, were the subject exposed to a continuous light pulse of the same intensity for this period, to phase shift the circadian pacemaker or treat the seasonal affective disorder in the subject, and structure for connecting the light emitter and control unit to a power source.

In one general embodiment, the light emitter is a strobe light. In another, such as for use with a pair of eyeshades, the device is a photodiode or photodiode array. The control unit is preferably operable to activate a light flash duration between about 1–25 msec, more preferably, between about 1–5 msec.

The control unit may include a timer for activating light flashes over a selected treatment period of preferably between 5 and 180 minutes.

For use in phase advancing or phase retarding the subject's circadian pacemaker, the control unit is designed to determine, from subject input about the extent and direction of circadian pacemaker phase change desired, the optimal treatment time. The unit may be designed to determine such optimal treatment time for each treatment at each of several successive days. It may also be operable to adjust light flash intensity and/or duration.

In a more specific aspect, the invention includes a portable eyeshade device for phase shifting the circadian pacemaker or treating seasonal affective disorder in a subject. The device includes an eyeshade mask adapted to worn by the subject, visible light emitters positioned within the mask to provide a light exposure to the subject's eyes, when the mask is being worn, a control unit for activating the light emitters to emit a light flash of a given intensity having a flash duration of between about 1–500 msec, at a periodicity of at least about one flash per minute, over a selected time period effective, were the subject exposed to a continuous light pulse of the same intensity for this period, to phase shift the circadian pacemaker or treat the seasonal affective disorder in the subject, and structure for connecting the light emitters and control unit to a power source.

These and other objects and features of the invention will become more fully apparent when the following detailed description of the invention is read in conjunction with the accompanying drawings.

DETAILED DESCRIPTION OF THE INVENTION

Figure 1:
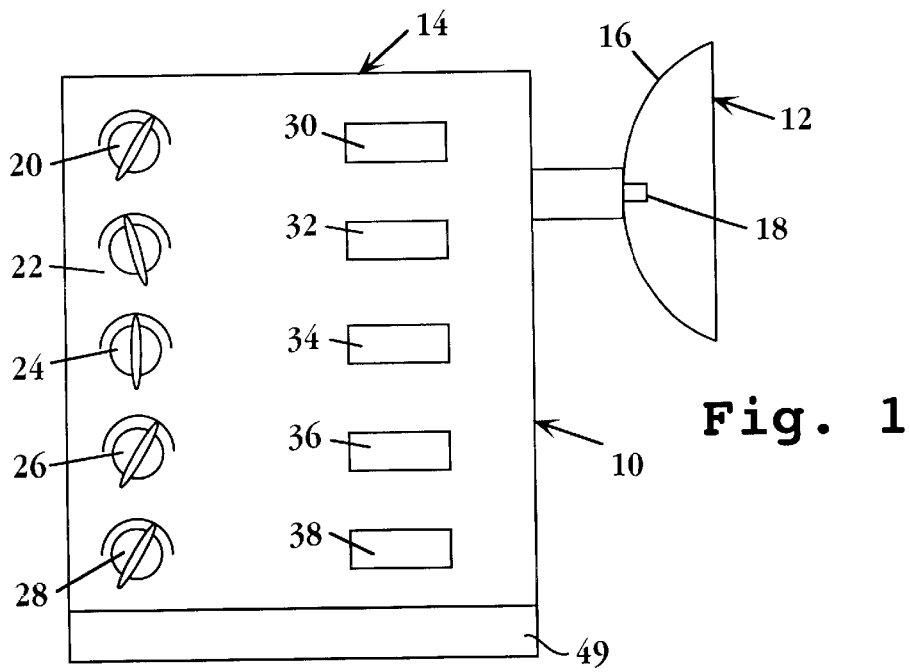
FIG. 1 shows a light-treatment device constructed according to one embodiment of the invention.

FIG. 1 shows a device 10 constructed according to one embodiment of the invention, for use in phase shifting the circadian pacemaker or treating seasonal affective disorder in a subject. The device includes a visible light emitter which in this embodiment is a strobe light or strobe light array 12 adapted to be supported in a position, such as one table or other support surface, for providing a light exposure to the subject's eyes. A control unit 14 in the device functions to activate the light emitter, to emit a light flash of a given intensity and duration, at a frequency of at least about one flash per minute.

Typically, the strobe light emitter has a parabolic reflector 16 and a high-intensity light flash source 18. In one preferred embodiment, the light flash source includes a plurality, e.g., four, separate light-flash sources, a selected number of which are fired in synchrony to vary the intensity of the flash over a several-fold intensity range, e.g., fourfold intensity. The emitter has a light flash duration of less than 500 msec, preferably between 1–25 msec, more preferably between 1–5 msec, e.g., 2 msec.

An exemplary strobe light emitter is a DynaLite Flash 2040 available commercially, having a light flash with about 2 msec duration, and an intensity of about 1–5 $\mu J/cm^2$, when measured at a distance of ten feet from the strobe light. As indicated above, the strobe light emitter may be modified to contain a plurality of light-flash units, to allow variation in light intensity over a severalfold range.

As shown in FIG. 1, unit 14 has controls 20, 22, 24, 26, and 28 for controlling (i) the light intensity of the emitter (control 20); (ii) the frequency of flash, i.e., number of flashes per minute (control 22); the total duration of treatment (control 24); the phase adjust between current circadian time and desired circadian time (control 26); and the current time local time (control 28). Also shown are display windows 30, 32, 34, 36, and 38 which display the settings for, or other information relating to controls 20, 22, 24, 26, and 28, respectively. The display windows may be standard liquid-crystal display devices.

Figure 2:
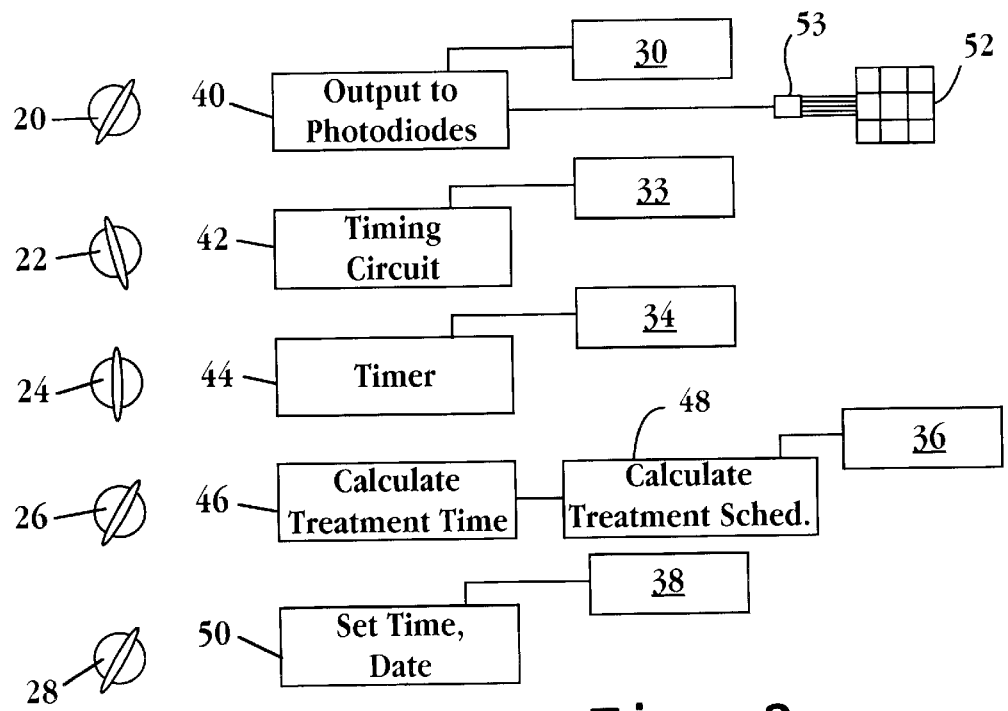
FIG. 2 illustrates operational features of a control unit in the light-treatment device of the invention.

Operational and functional elements of the control unit are shown in FIG. 2. Included here is an output circuit 40 responsive to the setting of intensity control 20 to supply a trigger signal to the light emitter, such as the nine-unit emitter shown at 52. Where, as here, light intensity is controlled by the number of emitter units that are triggered, the output circuit includes electronics hardware 53 designed to process the intensity of the trigger signal input and supply an activating signal to a selected number of the emitter units. The construction of the trigger circuitry, including the hardware for triggering a selected number of emitter units, to achieve a desired intensity level, is standard. The trigger circuit also displays the selected intensity at display window 30.

A timing circuit 42 in the control unit is responsive to the setting from frequency control 22, to signal the trigger circuit at a selected frequency. According to an important feature of the invention, and as discussed more fully below, the device operates through the timing circuit to provide a short light flash, e.g., 2 msec at a selected interval of every 5–60 secs (shorter and somewhat longer intervals may also be effective, as will be seen with reference to FIG. 4). The timing circuit provides is connected to the trigger circuit, to trigger a selected-intensity light flash at the selected frequency. The frequency selected may be displayed at the display window 32.

A timer 44 in the control unit is responsive to the selected duration of treatment selected through control 24. The duration of treatment will be set between a minimum of about 5 minutes, to a maximum of about 180 hours, and typically about 15–150 minutes. The timer circuit simply places the control unit in an "active" condition for the desired treatment length, maintaining the timing and trigger circuits active for the selected treatment period. The total selected treatment period, and/or the time of treatment remaining, may be displayed at display window 34. The control unit may also include a computational circuitry 46, e.g., a microprocessor, for calculating the optimal time of treatment in the subjects circadian rhythm, particular where the treatment is used to reset the subject's circadian rhythm to a new time zone. The calculation performed by circuitry 46 is based on user input concerning the time differential between old and new time zones. Exemplary time-of-treatment calculations, based on time zone difference, the subject's present circadian cycle, and the time of day in the new time zone will be given below. From such calculations, one skilled in the art will understand the construction of circuitry to perform the desired calculations.

As indicated in FIG. 2, the circuitry in the control unit may further include the circuit components, indicated at 48, designed to calculate a time-of-treatment regimen over a several day period, to gradually shift the subject's internal clock to the new time zone. Again, typical calculations will be given below.

The output of the calculation circuitry just described may be displayed at window 36 in a variety of display formats. For example, the window may display the current date and the optimal period to begin treatment for that date.

Alternatively, or in addition, the calculation circuitry may be connected to the timer in the control unit, to initiate treatment light flashes automatically at the optimal period of each day.

The calculation circuitry uses date and time data supplied to the control unit through control 28 and a set-time function 50. Local time and date may be displayed at window 38.

Device 10 also includes a power source 49 (FIG. 1), such as a battery, powering the light emitter and control unit. More generally, the device includes means for providing power to the unit and emitter, which may include a built-in battery source, or a power cord for connecting the device to an external AC or DC power source.

Figure 3:
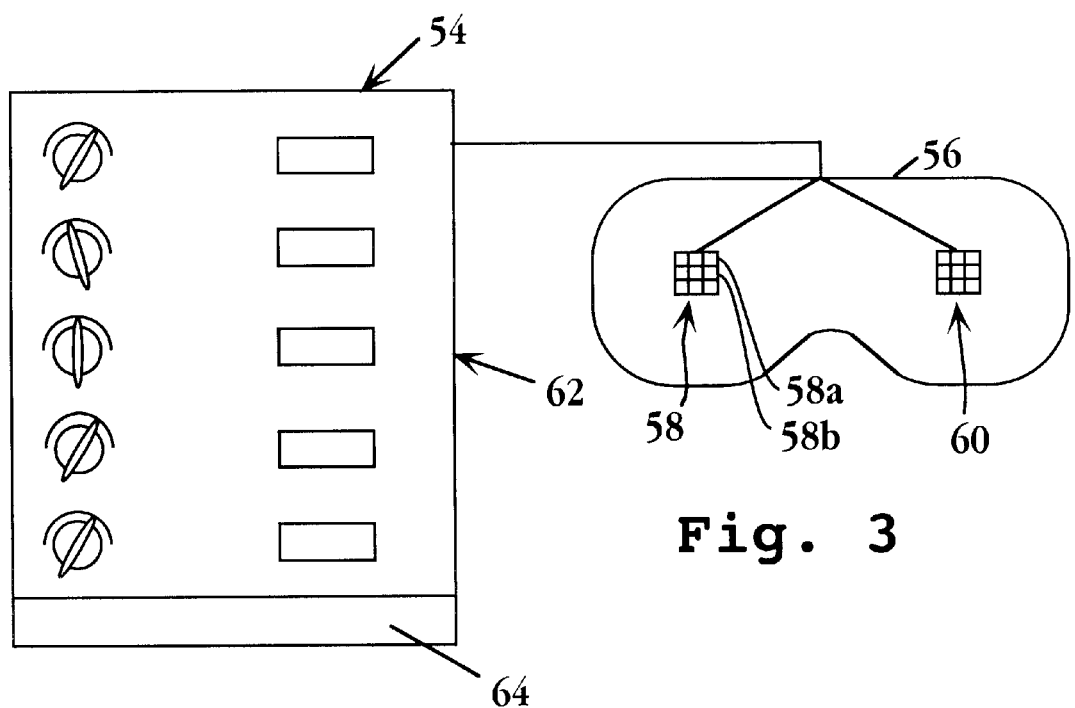
FIG. 3 shows a light-treatment device constructed according to another embodiment of the invention.

FIG. 3 illustrates an eyeshade light-treatment device 54 constructed according to another embodiment of the invention. The device has the general features and operation of device 10 above, but has the advantage that the light treatment is seen by the subject only, such as is appropriate for use on an airplane or in a darkened room.

Device 54 includes an eyeshade mask 56 to be worn by the user, and a pair of light emitters 58, 60 positioned on the mask to place the emitters next to the wearer's eyes. In the embodiment shown, each emitter, such as emitter 58, is composed of an array of photodiodes, in this case an array of nine photodiodes, such as photodiodes 58a, 58b. A selected number of these photodiodes are activated in synchrony, to vary light intensity over a nine-fold range, similar to the light-intensity variation described with respect to device 10.

Each photodiode in the array preferably has a flash intensity, e.g., maximum intensity when activated with a 1–5 msec trigger pulse, of between about 0.5–5 $\mu J/cm^2$. Thus, the intensity of each emitter array an be varied between about 0.5 and 50 $\mu J/cm^2$. The intensity variation is intended to allow adjustment of light intensity to a comfortable level for the user, and to effective levels when the user is receiving treatment with eyes closed, e.g., while sleeping.

Also included in device 54 is a control unit 62 powered by a battery 64, or connected to a suitable external power source through a power cord. The control unit has the general features, circuitry, and operation of unit 14 described above, including adjustment controls for flash intensity, frequency of light flash, duration of treatment, and phase adjust and date and time inputs. In one embodiment, the device is designed for traveller's use, having the eyeshades and a small, portable battery-powered control unit. In another general embodiment, e.g., for use in an airplane setting, the eyeshades may plug into a fixed control unit, e.g., the armrest of each passenger seat, with individually adjustable controls.

The devices just described are designed for practicing a novel light-treatment in accordance with another aspect of the invention. Heretofore, light treatment, either for treating SAD or for resetting a subject's circadian clock to a new time zone, has been carried out by exposing the subject to a constant-intensity light, or natural sunlight, over the entire treatment period, e.g., at least about 15 minutes of constant illumination. The theory behind the earlier treatment was that the retinal cells responsible for circadian reset required fairly unbroken levels of stimulation.

Figure 4:
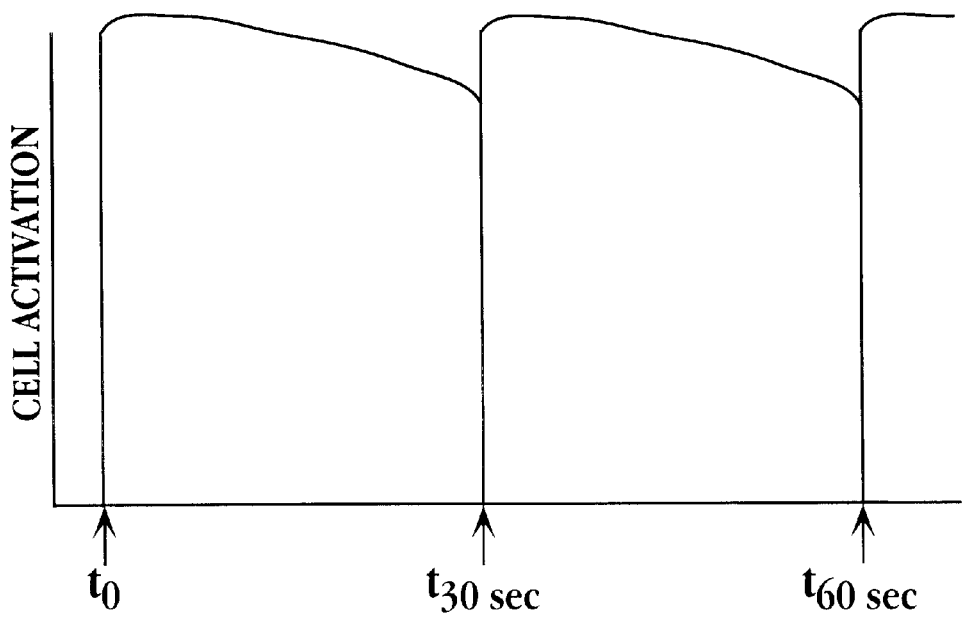
FIG. 4 illustrates the apparent light-response behavior of light-activated neuronal cells involved in circadian rhythm reset, in accordance with the invention.

The method of the present invention is based on the discovery that the circadian system in mammals has a memory for light flashes, of up to one minute or more, allowing the system to integrate the stimulation over an extended treatment method, by exposing a subject's eyes to brief intermittent light flashes over the same period. FIG. 4 illustrates the hypothesized light-memory effect. The curve in the figure represents the level of activation of the cells responsible for registering light information from retinal stimulation. As seen, an instantaneous light burst, such as given at time $t_0$, causes the cells to quickly reach a maximal activation level, then decay slowly over a "dark" period. If the retina is exposed to a second burst within a period of up to 30–60 secs, the cells quickly return to maximal activation level, and begin a slow decay again during a dark period of up to one minute. By successively stimulating the cells every 5–60 seconds, the cells are able to integrate the entraining light signals from one light pulse to another, as if the subject were exposed to a relatively constant illumination, even though the total illumination time for the treatment may be as low as 60–600 msec.

Applying this discovery, the operation of the above device to the light-treatment method of the invention can be appreciated. The basic variables of the method are time of day for treatment, light intensity, light flash duration, frequency of light flashes, and treatment duration. The following provides some general guidelines in selecting these variables:

1. Time of day for treatment. The treatment type and purpose will establish the optimal time of day for light treatment. For example, in the treatment of seasonal affective disorder, the optimal time to begin treatment is in the early morning hours, corresponding roughly to the circadian time $CT_{22}$–$CT_{24}$, i.e., during the last part of the subject's circadian period, immediately before the circadian period corresponding to normal daylight hours of the person, assuming a photoperiod of 12 hours of light, 12 hours of darkness. Typically treatment is begun anywhere from between 5 and 8 AM, and is continued for a treatment period of at least about 5 minutes, generally 5–150 minutes, and typically 15–30 minutes. The treatment may be given 2–3 times a week, and is most effective when the same treatment hours are used from one session to the next.

For resetting the subject's circadian clock to a new time zone, optimal treatment time for circadian clock reset is based on the following principles:

(i) To reset in a forward direction, i.e., where the time zone is 12 hours or less in a later-time direction with respect to the accustomed time zone, light treatment is given over the subjects's circadian time $CT_{18}$–$CT_{24}$, and preferably $CT_{22}$–$CT_{24}$ (ii) to reset in the opposite direction, i.e., where the time zone is 12 hours or less in an earlier-time direction with respect to the accustomed time zone, light treatment is given over the subjects's circadian time $CT_{12}$–$CT_{18}$, and preferably $CT_{12}$–$CT_{14}$;

(iii) the optimal treatment time is early morning; and (iv) the treatment time may be gradually shifted over a period of 2–3 successive days from the middle of the subject's $CT_{12}$–$CT_{24}$ toward either extreme, i.e., $CT_{12}$ in the case of a shift to an earlier-time zone, or $CT_{24}$ in the case of a shift to a later-time zone.

2. Flash intensity. An effective light intensity will depend primarily on the background lighting in the room, and the distance of the light emitter from the user's eyes. With lower room lighting, the user's eyes will be more "dark-adjusted", and require substantially less light intensity than in a room with normal lighting. Since light intensity falls off as the square root of distance from the illumination source, the between the light emitter and subject's eyes will have a critical effect on the amount of light stimulus received by the user. Preferably, these two variables are controlled in the following way. The light emitter is first placed a selected known distance, e.g., 1–5 feet from the user's face. A light meter in the control unit (not shown) then measure ambient lighting and adjusts the light flash intensity accordingly. An optimal light intensity can be refined and optimized, for example, over a period of continued use, to achieve a level that is found to be most therapeutic. As a general guide, the light intensity should correspond to an illumination level of between about 1–100 $\mu J/cm^2$, depending on the level of background lighting, in the case of the external light flash device, and whether the subject has open or closed eyes, in the case of the eyeshade embodiment.

More generally, the intensity corresponds roughly to light intensity used for conventional constant-illumination light therapy, but where the light exposure is in bursts of typically 1–5 msec, at intervals of up to 1 burst per minute.

3. Flash duration. The device described will preferably have a default flash duration of 1–5 msec, typically 2 msec. Although longer flash durations are possible, e.g., up to 500 msec or more, an advantage of the present invention is that light therapy can be effectively administered with a very low total light exposure time, e.g., 120–600 msec.

4. Flash frequency and treatment duration. Studies conducted in support of the present invention have shown significant reset of circadian clock in mammals maintained in a dark environment, and therefore with free-running circadian clocks, with flash treatment for as little as five minutes, employing a 2 msec flash frequency of 12 flashes/minute (total of 120 msec of exposure). Similar results were achieved by 2 msec light stimulation of one flash/minute over a 60 minute period (120 msec of exposure). Typically, the treatment time will be at least 15 minutes, with the frequency of flashes set to produce at least about 120–600 msec of exposure, with a 2 msec flash duration.

More generally, the duration of treatment, in relation to light-flash intensity, is such as to produce an effective therapy were the subject exposed to a continuous light pulse of the same intensity for this period, to phase shift the circadian pacemaker or treat the seasonal affective disorder in the subject.

With these basic guidelines, it will be appreciated how the external-light or eyeshade device described above operates in the light-treatment method. Operation will be described with respect to device 10, it being understood that the same treatment variables and control-unit operation applies to both types of devices, e.g., where the light is emitted in the direction of the user in a room, or where the light is emitted adjacent the user's eyes in an eyeshade device.

As a first setting variable, the type and purpose of the light treatment is established. The control unit will then determine a desired treatment time. The user may select a treatment time and flash frequency, or the unit may select default conditions, e.g., one flash every 30 seconds for 1.5 hours, and let the user adjust these variables over time for maximum therapeutic benefit.

Light treatment for SAD may be continued over a several-day, several-week, or several-month period, depending on length of light deprivation, and the time needed to synchronize and maintain the subject's circadian cycles with normal light/dark cycles. The treatment times for circadian reset for a new time zone will typically be a graduated reset over a 2–4 day period, as outlined above.

From the foregoing, it will be appreciated that the intermittent light-flash treatment method of the invention, and the device for use in practicing the method, offer several advantages over previous light treatments with a constant light intensity. Treatment involving the external strobe light device allows the user to carry out various sedentary activities, such as reading, watching TV, or studying, without the distraction of a constant high-intensity room light. The strobe device is portable, less expensive, and much more energy efficient than a bank of high intensity lights.

The eyeshade device allows the user to receive light therapy without interrupting others, such as in an airplane, or a darkened room. The eyeshade device can be made portable for travellers, and the relatively small energy demand allows the device to be powered with a small dry-cell battery.

The calculation circuitry in the device provides the user with optimized treatment times and duration, based on simple user inputs, such as time of day and, for circadian clock reset, the difference between old and new time zones.

Although the invention has been described with respect to particular embodiments, it will be appreciated that various changes and modifications can be made without departing from the invention.

It is claimed:

1. A method of phase shifting the circadian pacemaker or treating seasonal affective disorder in a subject, comprising exposing the subject's eye region to a given-intensity light flash having a flash duration of between about 1–500 msec, at a periodicity of at least about one flash per minute, over a time period between about 15 and 150 minutes, carried out during hour 18 to hour 24 or hour 12 to hour 18 of the subject's circadian time effective, were the subject exposed to a continuous light pulse of the same intensity for this period, to phase shift the circadian pacemaker or treat the seasonal affective disorder in the subject.

2. The method of claim 1, wherein the light flash duration is between about 1–25 msec.

3. The method of claim 1, wherein the light flash duration is between about 1–5 msec.

* * * * *